(12) United States Patent
Caparso et al.

(10) Patent No.: US 8,036,750 B2
(45) Date of Patent: Oct. 11, 2011

(54) SYSTEM FOR NEURAL CONTROL OF RESPIRATION

(75) Inventors: Anthony Caparso, St. Louis Park, MN (US); Imad Libbus, St. Paul, MN (US); M. Jason Brooke, Minneapolis, MN (US); Kent Lee, Shoreview, MN (US); Jonathan Kwok, Shoreview, MN (US); Yachuan Pu, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 386 days.

(21) Appl. No.: 11/151,122

(22) Filed: Jun. 13, 2005

(65) Prior Publication Data

US 2006/0282131 A1    Dec. 14, 2006

(51) Int. Cl.
*A61N 1/18* (2006.01)
(52) U.S. Cl. .......................................... 607/42; 607/118
(58) Field of Classification Search ............ 607/42, 607/118
See application file for complete search history.

(56) References Cited

U.S. PATENT DOCUMENTS

| | | | |
|---|---|---|---|
| 5,483,969 A | 1/1996 | Testerman et al. | |
| 5,485,851 A | 1/1996 | Erickson | |
| 5,522,862 A | 6/1996 | Testerman et al. | |
| 5,540,733 A | 7/1996 | Testerman et al. | |
| 5,546,952 A | 8/1996 | Erickson | |
| 5,549,655 A | 8/1996 | Erickson | |
| 6,587,725 B1 * | 7/2003 | Durand et al. | 607/42 |
| 6,633,779 B1 * | 10/2003 | Lee et al. | 607/42 |
| 7,155,278 B2 * | 12/2006 | King et al. | 607/2 |
| 2005/0043772 A1 * | 2/2005 | Stahmann et al. | 607/42 |
| 2005/0061320 A1 | 3/2005 | Lee et al. | |
| 2005/0085866 A1 | 4/2005 | Tehrani | |
| 2005/0085868 A1 * | 4/2005 | Tehrani et al. | 607/42 |
| 2006/0224211 A1 * | 10/2006 | Durand et al. | 607/48 |

FOREIGN PATENT DOCUMENTS

| | | |
|---|---|---|
| EP | 1308181 | 5/2003 |
| EP | 1308181 A2 | 5/2003 |
| EP | 1393773 | 3/2004 |

(Continued)

OTHER PUBLICATIONS

"International Search Report and Written Opinion for Application No. PCT/US2006/021323, Date mailed Oct. 20, 2006", 13 Pages.

(Continued)

*Primary Examiner* — Niketa I Patel
*Assistant Examiner* — Joseph Stoklosa
(74) *Attorney, Agent, or Firm* — Schwegman, Lundberg & Woessner, P.A.

(57) ABSTRACT

A system, device and method for neural control of respiration are provided. One aspect of this disclosure relates to an implantable medical device for sensing and controlling respiration during incidence of central respiratory diseases. According to various embodiments, the device includes a sensing circuit to receive sensed signals representative of an incidence of a central respiratory disease. The device also includes a neural stimulator adapted to generate neural stimulation signals, and a controller to communicate with the sensing circuit and to control the neural stimulator to stimulate a desired neural target in response to the detection of the incidence of a central respiratory disease. In an embodiment, the device includes a plurality of sensors which are adapted to monitor physiological parameters to detect the incidence of a central respiratory disease and to send signals to the sensing circuit. Other aspects and embodiments are provided herein.

25 Claims, 5 Drawing Sheets

FOREIGN PATENT DOCUMENTS

| | | |
|---|---|---|
| EP | 1393773 A1 | 3/2004 |
| WO | WO 0141868 A1 | 6/2001 |
| WO | WO-2001041868 A1 | 6/2001 |
| WO | WO-2003096882 A1 | 11/2003 |

OTHER PUBLICATIONS

"European Application Serial No. 06771862.7, Communication mailed Jun. 13, 2008", 5 pgs.

"European Application Serial No. 06771862.7, Response filed Dec. 23, 2008 to Communication mailed Jun. 13, 2008", 3 pgs.

"European Application Serial No. 06771862.7, Result of Consultation dated Jan. 25, 2010", 4 pgs.

Bray, J. J, et al., *Human Physiology*, (4th Edition, Blackwell Science), 454-463.

"European Application U.S. Appl. No. 10176902.4, Extended European Search Report mailed Dec. 27, 2010", 8 pgs.

Bray, John J, "", Human Physiology, Blackwell Science, UK; ISBN: 0-86542-775-5, (1999), pp. 454-463.

"European Application Serial No. 10176902A, Response filed Jul. 21, 2011 to European Search Report dated Dec. 27, 2010", 10 pgs.

\* cited by examiner

SYSTEM FOR NEURAL CONTROL OF RESPIRATION

TECHNICAL FIELD

This disclosure relates generally to implantable medical devices and, more particularly, to systems, devices and methods for neural control of respiration to treat central respiratory diseases.

BACKGROUND

Central respiratory diseases include disorders that affect breathing during sleep or while a person is awake. Central respiratory diseases are associated with incorrect sensing of carbon dioxide or oxygen levels in the blood. If nerve receptors do not send the correct neural signals, in essence deceiving the brain by reporting incorrect levels of carbon dioxide or oxygen, an incidence of a central respiratory disease can occur. The brain responds by slowing breathing, and even ceasing breathing in extreme cases.

Respiratory disorders during sleep and during the day include central sleep apnea or hypopnea and periodic breathing or dyspnea, respectively. Central sleep apnea refers to the cessation of breathing during sleep, and hypopnea refers to abnormally slow or shallow breathing during sleep. Both conditions have serious health consequences, including association with cardiac arrhythmias.

SUMMARY

The above-mentioned problems and others not expressly discussed herein are addressed by the present subject matter and will be understood by reading and studying this specification.

Disclosed herein, among other things, is an implantable medical device (IMD) for sensing and controlling respiration to treat central respiratory diseases. According to various embodiments, the device includes a sensing circuit to receive sensed signals representative of an incidence of a central respiratory disease. The device also includes a neural stimulator adapted to generate neural stimulation signals, and a controller to communicate with the sensing circuit and to control the neural stimulator to stimulate a desired neural target in response to the detection of the incidence of a central respiratory disease. In an embodiment, the device includes a plurality of sensors which are adapted to monitor physiological parameters to detect the incidence of a central respiratory disease and to send signals to the sensing circuit.

One aspect of this disclosure relates to a system for neural control of respiration during disordered breathing. According to various embodiments, the system includes at least one neural stimulation lead having at least one electrode, and at least one sensor adapted to monitor physiological parameters to detect the incidence of a central respiratory disease. The system also includes an implantable medical device (IMD) coupled to the at least one lead and to the at least one sensor. The IMD includes a sensing circuit to receive sensed signals representative of an incidence of a central respiratory disease, a neural stimulator adapted to generate neural stimulation signals, and a controller to communicate with the sensing circuit and to control the neural stimulator to stimulate a desired neural target in response to the detection of the incidence of a central respiratory disease. According to one embodiment, the sensed signals include signals representative of neural activity for chemoreceptors (CR) and mechanoreceptors (MR), and in response the neural stimulator stimulates nerves associated with CR and MR to treat central respiratory disease.

Various system embodiments include a means for sensing at least one physiological parameter to detect an incidence of a central respiratory disease and means for delivering neural stimulation therapy to mimic normal CR and MR activity, based on the at least one sensed physiological parameters. According to an embodiment, the means for delivering neural stimulation therapy includes a nerve cuff electrode. According to an embodiment, the means for delivering neural stimulation therapy includes a transvascular stimulation lead.

One aspect of this disclosure relates to a method for sensing and controlling respiration during central respiratory disease. Various embodiments of the method include sensing one or more physiological parameters to detect an incidence of a central respiratory disease. The method also includes comparing the sensed parameters to a desired value range for the sensed parameters. The method further includes delivering neural stimulation therapy to mimic normal CR and MR activity, if one or more of the sensed parameters is not within the desired range.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

Central respiratory diseases are associated with nerve receptors that do not send the correct neural signals, in essence deceiving the brain by reporting incorrect levels of carbon dioxide or oxygen. Neural signals for respiration are disrupted, either at the level of the receptor, at the peripheral nerve fibers, or at central synapses. The brain responds by augmenting breathing, and even ceasing breathing in extreme cases. Central sleep apnea, as an example, can be a consequence of chronic heart failure or neuromuscular disease such as stroke or spinal cord injury. An implantable system to reduce or eliminate incidence of central respiratory diseases is needed.

The present system is capable of treating and preventing central respiratory diseases, including the disordered breathing conditions of central sleep apnea and hypopnea (referred to generally as sleep disordered breathing), or central hypoventilation or central hyperventilation, using an IMD. One embodiment of the device monitors physiological parameters including neural activity to detect the incidence of a central respiratory disease. When disordered breathing is detected, stimulation is applied downstream from the disruption in the neural pathway to CRs or MRs, to nerves that carry respiration receptor signals, to the area of the brain that controls receptor information, or to various combinations thereof. The stimulation mimics the neural activity of healthy CRs and MRs by regulating the afferent and efferent neural drive from respiration receptors to the diaphragm, ending the event. Various embodiments provide feedback for a closed loop system. Feedback can be provided by tidal volume or rate information, in various embodiments.

Implantable Medical Device

Figure 1:
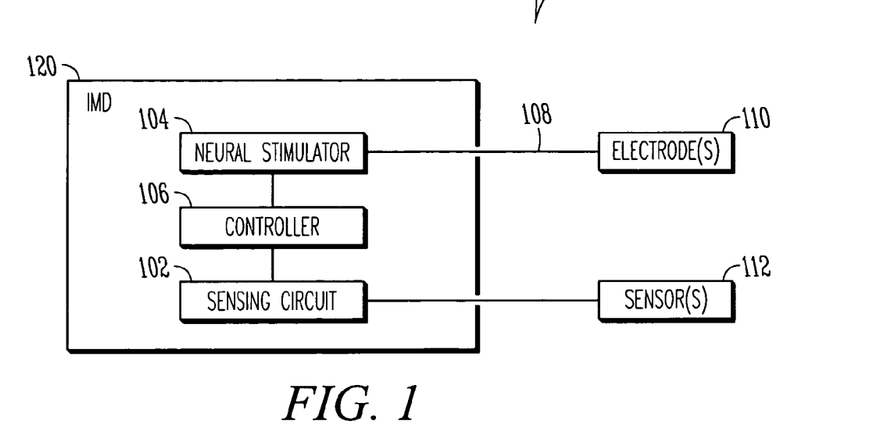
FIG. 1 illustrates a system for sensing and controlling respiration to treat central respiratory disease, according to one embodiment.

FIG. 1 illustrates a system 100 for sensing and controlling respiration to treat central respiratory disease, according to one embodiment. The system includes an implantable medical device 120 for neural control of respiration to treat central respiratory disease. The device 120 includes a sensing circuit 102 to receive sensed signals representative of an incidence of a central respiratory disease. The device also includes a neural stimulator 104 adapted to generate neural stimulation signals, and a controller 106 to communicate with the sensing circuit 102 and to control the neural stimulator 104 to stimulate a desired target in response to the detection of the incidence of a central respiratory disease.

According to an embodiment, the sensed signals include signals representative of neural activity for CRs and MRs, and in response the neural stimulator is adapted to stimulate nerves associated with CRs and MRs to treat central respiratory disease. The device may stimulate the same or different CRs and MRs than those sensed by the sensors.

System for Sensing and Controlling Respiration

The system 100 depicted in FIG. 1 includes at least one neural stimulation lead 108 having at least one electrode 110, and at least one sensor 112 adapted to monitor physiological parameters to detect the incidence of a central respiratory disease. The system 100 also includes the implantable medical device 120 coupled to the at least one lead 108 and to the at least one sensor 112. According to an embodiment, the device 120 is connected to the at least one sensor 112 via a lead 109. According to an embodiment, the device 120 is connected to the at least one sensor 112 via a wireless connection.

As discussed above, the implantable device 120 includes a sensing circuit 102 to receive sensed signals representative of an incidence of a central respiratory disease, a neural stimulator 104 adapted to generate neural stimulation signals, and a controller 106 to communicate with the sensing circuit and to control the neural stimulator to stimulate a desired neural target in response to the detection of the incidence of a central respiratory disease. According to one embodiment, the sensed signals include signals representative of neural activity for CRs and MRs, and in response the neural stimulator 104 stimulates nerves associated with CRs and MRs to treat a central respiratory disease. The implantable medical device is also adapted to provide cardiac rhythm management (CRM) therapy, such as cardiac pacing, atrial or ventricular defibrillation, and cardiac resynchronization therapy, in an embodiment. According to an embodiment, this system is implemented in a subcutaneous configuration, with or without additional CRM capabilities. According to an embodiment, the lead 108 includes a nerve cuff. According to an embodiment, the lead 108 includes a transvascular stimulation lead. Other embodiments of the lead 108 are within the scope of this disclosure.

Figure 2A:
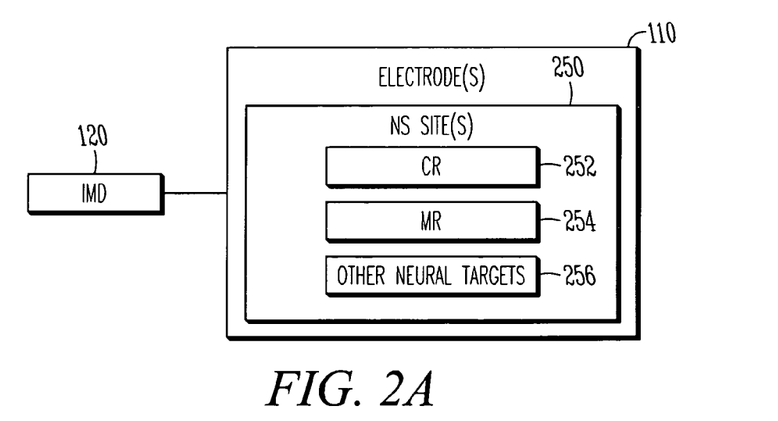
FIG. 2A illustrates an electrode configuration for the system, according to various embodiments.

FIG. 2A illustrates an electrode configuration for the system, according to various embodiments. The electrodes 110 are adapted to deliver neural stimulation from the neural stimulator to neural stimulation (NS) site(s) 250 in the body. In an embodiment, the neural stimulator is adapted to stimulate CRs 252. In an embodiment, the neural stimulator is adapted to stimulate MRs 254. According to various embodiments, the neural stimulator is adapted to stimulate other targets 256, such as peripheral nerves, a vagal nerve, a glossopharyngeal nerve, a phrenic nerve, intercostals muscles, respiratory centers in the brain, and/or a diaphragm muscle to treat disordered breathing. Other targets are within the scope of this disclosure, and are discussed with respect to FIG. 3B below.

Figure 2B:
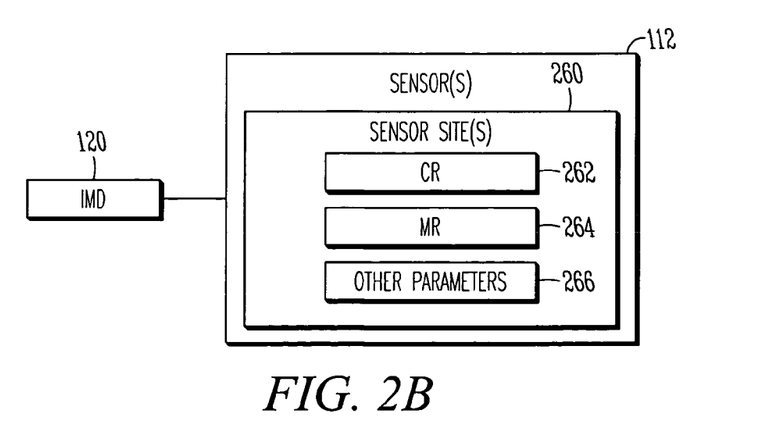
FIG. 2B illustrates a sensor configuration for the system, according to various embodiments.

FIG. 2B illustrates a sensor configuration for the system, according to various embodiments. The sensors 112 are adapted to monitor various physiological parameters to detect the incidence of a central respiratory disease. In various embodiments, the sensors 112 monitor one or more sensor site(s) 260. In an embodiment, the at least one sensor 112 is adapted to monitor neural activity of CRs 262. In an embodiment, the at least one sensor 112 is adapted to monitor neural activity of MRs 264. In various embodiments, the at least one sensor 112 is adapted to monitor other parameters 266, such as body movement, heart rate, QT interval, eye movement, respiration rate, transthoracic impedance, tidal volume, minute ventilation, body posture, an electroencephalogram (EEG), an electrocardiogram (ECG), an electrooculogram (EOG), an electromyogram (EMG), an electroneurogram (ENG), muscle tone, body temperature, pulse oximetry, carbon dioxide levels, blood gas, and/or time of day. In an embodiment, the at least one sensor 112 includes a blood gas sensor for taking direct measurement of carbon dioxide and oxygen. In an embodiment, the at least one sensor 112 includes a sensor external to a human body. Other sensed parameters are within the scope of this disclosure.

The sensors 112 include those directly connected to an implantable medical device (IMD) 120 via a lead, in an embodiment. In various embodiments, the sensors 112 are inside or on the surface of the IMD 120. In various embodiments, the sensors 112 communicate with the IMD 120 using wireless communications.

The present system uses a combination of any or all of these signals to determine the onset of a central respiratory disease, such as disordered breathing, central hypoventilation or central hyperventilation. If an onset is detected, neural stimulation is applied through the at least one lead to receptors directly, to the afferent nerves from the receptors, or to the respiration area of the brain, either directly or indirectly. Stimulation is applied to mimic normal receptor activity while all feedback signals are within normal ranges. The neural resetting of the receptor signal allows the brain to normally control respiration. According to an embodiment, the parameters (frequency, amplitude, pulse width, etc.) used for stimulation are set based on all sensor feedback received from the sensors 112. If neural signals from the receptors are lost, the implantable medical device 120 can provide artificial signals within normal ranges to provide respiration control. If respiration control is lost, the device 120 is able to control breathing by stimulation of the phrenic nerve, diaphragm or intercostals muscle. The parameters (frequency, amplitude, pulse width, etc.) for this stimulation are based on feedback from the physiological sensors 112.

One aspect of this disclosure relates to a system for sensing and controlling respiration during disordered breathing. The system includes means for sensing at least one physiological parameter to detect an incidence of central apnea/hypopnea and means for delivering neural stimulation therapy to mimic normal CR and MR activity, based on the at least one sensed physiological parameters. The means for sensing one or more physiological parameters includes means for sensing of neural activity for CRs and MRs in an embodiment. Feedback is provided through sensing tidal volume and rate information, according to various embodiments. According to an embodiment, the means for delivering neural stimulation therapy includes a nerve cuff electrode. According to an embodiment, the means for delivering neural stimulation therapy includes a transvascular stimulation lead.

Neural Stimulation for Controlling Respiration

Figure 3A:
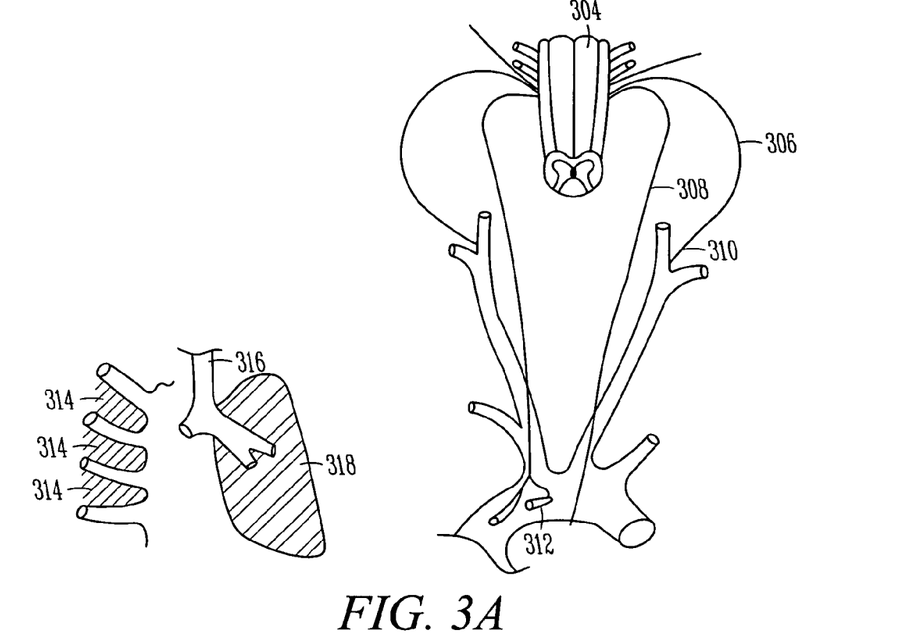
FIG. 3A illustrates neural physiology of a human respiratory system.

FIG. 3A illustrates neural physiology of a human respiratory system. The diagram depicts a medulla 304, a glossopharyngeal nerve 306, a vagus nerve 308, a carotid body 310, aortic bodies 312, intercostals muscles 314, extra-pulmonary airways 316, and lungs 318. Sensing nerves related to control of respiration includes sensory input from a number of sensors. Central CRs are sensed in an embodiment. These include a central surface of the medulla close to the site of exit of the ninth and tenth cranial nerves. Peripheral CRs are sensed in an embodiment. These include aortic and carotid bodies not associated with the carotid baroreceptors, and which respond to $pO_2$, $pCO_2$ and pH.

In an embodiment MRs in the lungs, including pulmonary stretch receptors, irritant receptors, and unmyelinated C-fibers, are sensed. Pulmonary stretch receptors and irritant receptors are common in the smooth muscle layer of extra-pulmonary airways 316. C-fibers are common in the lung 318 interstitium and alveolar wall. Other examples of MR sites include intercostals muscle 314 spindles fibers and baroreceptors. Other locations to sense nerves related to control of respiration, including detection of central respiratory diseases such as hypopnea, central apnea, hyperventilation or hypoventilation are within the scope of this disclosure.

An incidence of central respiratory disease using sensed CR and MR information can be detected in a number of ways. In an embodiment, the measured gain of the signal is not within a normal range, which provides an indication of an incidence of central respiratory disease. In an embodiment, the measured delay of the signal is not within a normal rage, providing an indication of an incidence of central respiratory disease. Other detection methods using CR and MR sensed information are within the scope of this disclosure.

Figure 3B:
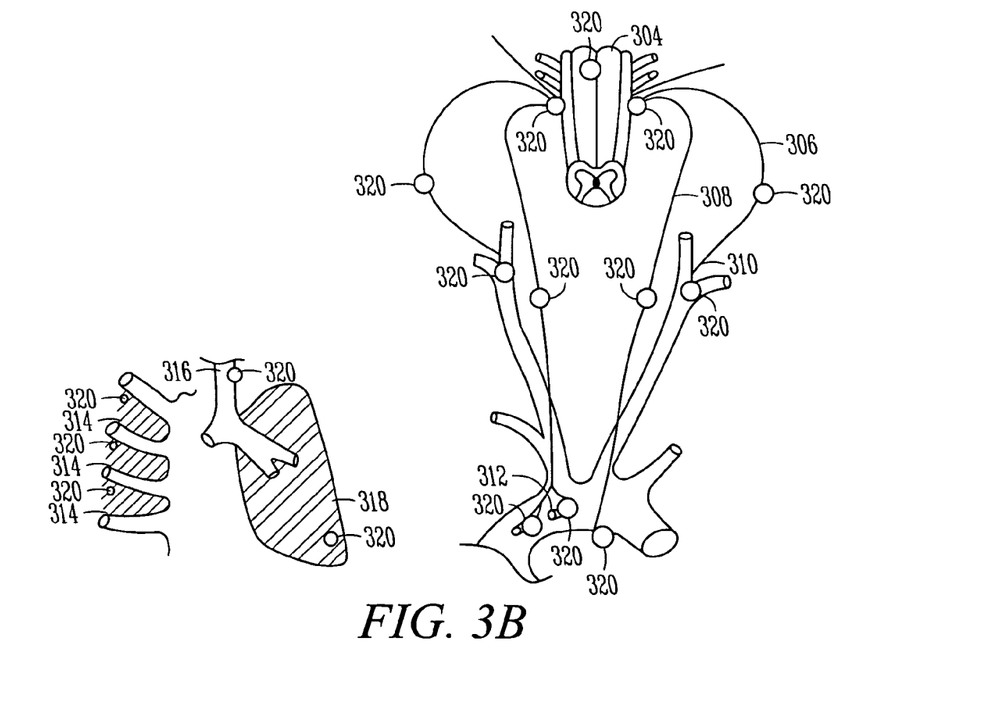
FIG. 3B illustrates neural stimulation targets for controlling respiration, according to various embodiments.

FIG. 3B illustrates neural stimulation targets for controlling respiration, according to various embodiments. Locations 320 for neural stimulation to prevent or end central respiratory diseases such as central apnea are depicted. These locations 320 include along the medulla 304, along the glossopharyngeal nerve 306, along the vagus nerve 308, along the carotid body 310, along the aortic bodies 312, along the intercostals muscles 314 spindle fibers, along the smooth muscle of the extra-pulmonary airways 316, and along the unmyelinated C-fibers of the lung 318 interstitium. Additional locations for neural stimulation include a phrenic nerve location, a lung mechanoreceptor location or a diaphragm muscle location, according to various embodiments. Other locations to provide neural stimulation to prevent or end central respiratory diseases are within the scope of this disclosure. According to various embodiments, selective activation of nerves (such as the vagus nerve in an embodiment) is used to prevent or end central sleep apnea or hypopnea.

Implantable System and External Programmer

Figure 4:
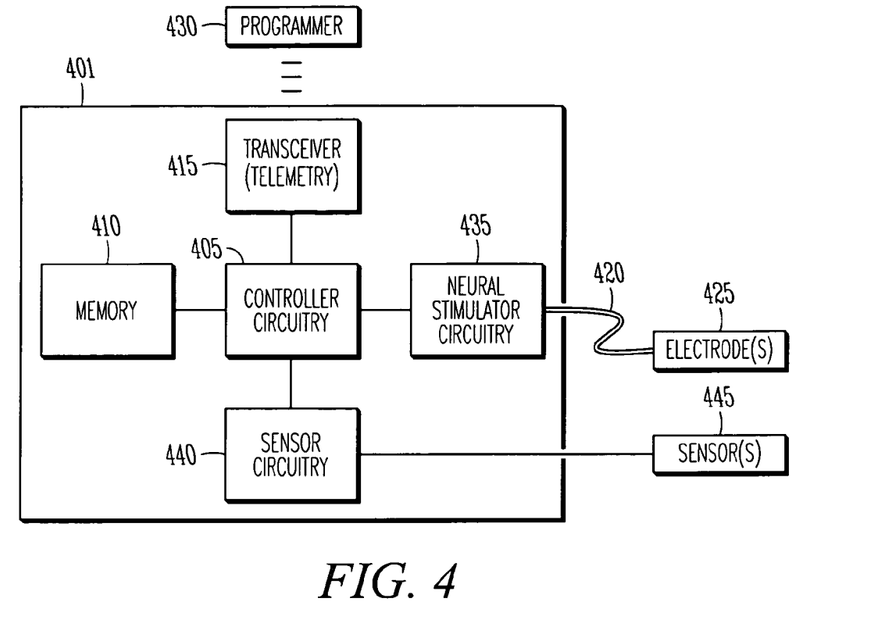
FIG. 4 is a schematic illustration of an implantable system for neural control of respiration to treat central respiratory disease, according to one embodiment.

FIG. 4 is a schematic illustration of an implantable system for neural control of respiration to treat central respiratory disease, according to one embodiment. The system includes an implantable medical device (IMD) 401, an electrical lead 420 coupled to the IMD 401, and at least one electrode 425. The IMD includes a controller circuit 405, a memory circuit 410, a telemetry circuit 415, and a neural stimulation circuit 435. The controller circuit 405 is operable on instructions stored in the memory circuit to deliver an electrical neural stimulation therapy. Therapy is delivered by the neural stimulation circuit 435 through the lead 420 and the electrode(s) 425. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 senses one or more physiological parameters to detect an incidence of a central respiratory disease, compares the sensed parameters to a desired value range for the sensed parameters, and delivers neural stimulation therapy if one or more of the sensed parameters is not within the desired range, as disclosed in the method depicted in FIG. 6, described below. The illustrated system also includes sensor circuitry 440 that is coupled to at least one sensor 445. The controller circuit 405 processes sensor data from the sensor circuitry and delivers a therapy responsive to the sensor data.

The electrical lead 420 includes a direct stimulation lead for providing stimulation directly to a nerve trunk, according to one embodiment. An example of a direct stimulation lead includes a lead with a nerve cuff. In an embodiment, the at least one neural stimulation lead 420 includes an indirect stimulation lead for providing stimulation indirectly to a nerve trunk, through the wall of an adjacent blood vessel. Examples of indirect stimulation leads include chronically implanted transvascular neural stimulation leads.

Figure 5:
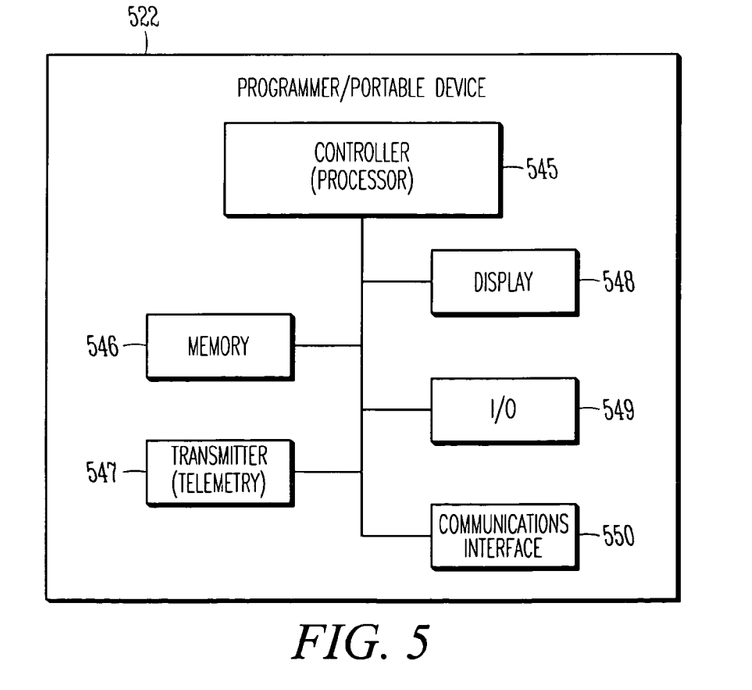
FIG. 5 illustrates a programmer such as illustrated in the system of FIG. 4 or other external device to communicate with the implantable medical device(s), according to one embodiment.

FIG. 5 illustrates a programmer 522, such as the programmer 430 illustrated in the system of FIG. 4 or other external device to communicate with the implantable medical device (s), according to one embodiment. An example of another external device includes Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Figure 6:
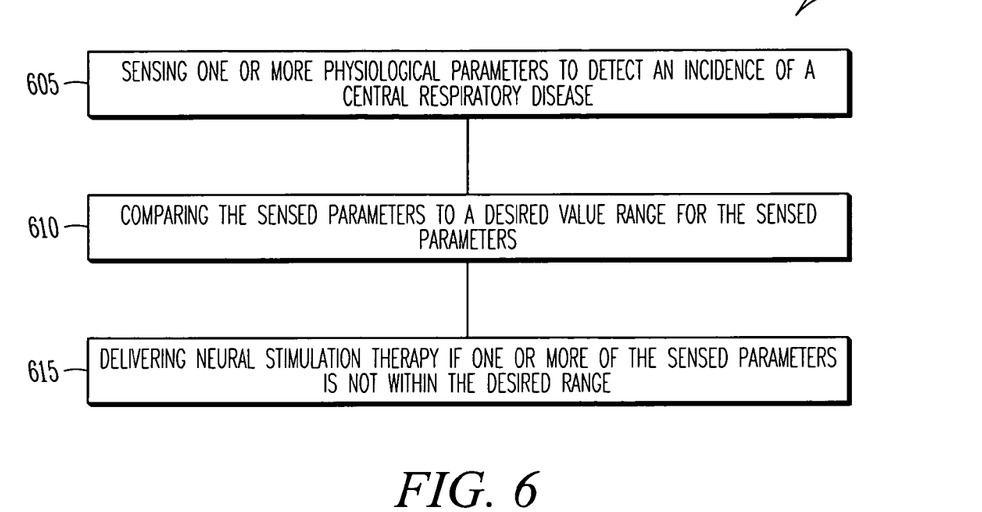
FIG. 6 illustrates a flow diagram of a method for sensing and controlling respiration to treat central respiratory disease, according to one embodiment.

Method for Sensing and Controlling Respiration to Treat Central Respiratory Disease FIG. 6 illustrates a flow diagram of a method for sensing and controlling respiration to treat central respiratory disease, according to one embodiment. The method 600 includes sensing one or more physiological parameters to detect an incidence of a central respiratory disease, at 605. The method also includes comparing the sensed parameters to a desired value range for the sensed parameters, at 610. The method further includes delivering neural stimulation therapy to mimic normal CR and MR activity, if one or more of the sensed parameters is not within the desired range, at 615.

Stimulation is applied to mimic normal receptor activity while all feedback signals are within normal ranges. The neural resetting of the receptor signal allows the brain to normally control respiration. According to an embodiment, the parameters (frequency, amplitude, pulse width, etc.) used for stimulation are set based on all sensor feedback received from the sensors.

Figure 7A:
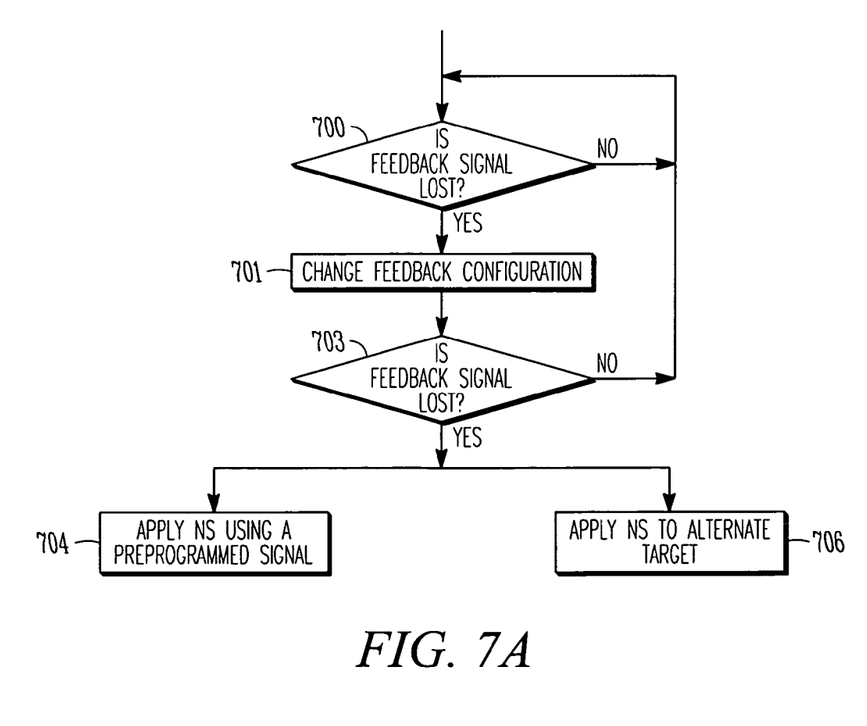
FIG. 7A illustrates a flow diagram of a method for responding to a lost feedback signal, according to various embodiments.

FIG. 7A illustrates a flow diagram of a method for responding to a lost feedback signal, according to various embodiments. At 700, if a feedback signal is lost or unavailable, sensor feedback configuration is changed at 701. If feedback signal is still unavailable at 703, in one embodiment neural stimulation therapy is applied using a preprogrammed stimulation signal at 704. In this way, if neural signals from the receptors are lost, the implantable medical device will provide artificial signals within normal ranges to provide respiration control. An embodiment involves delivering neural stimulation therapy to an alternative neural target if a feedback signal is not available, at 706. Not all embodiments use all the described steps.

Figure 7B:
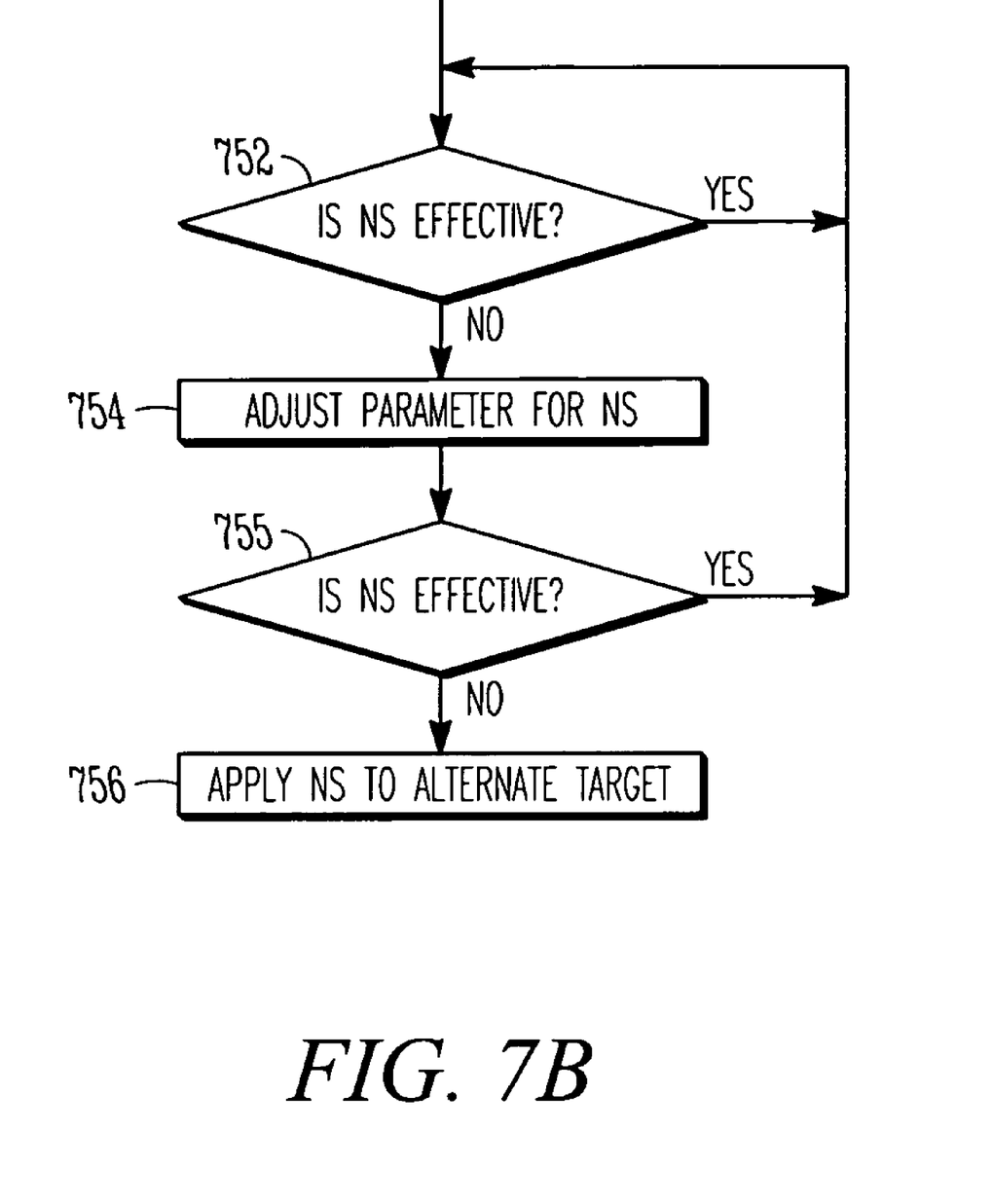
FIG. 7B illustrates a flow diagram of a method for responding to ineffective neural stimulation, according to various embodiments.

FIG. 7B illustrates a flow diagram of a method for responding to ineffective neural stimulation, according to various embodiments. If respiration control is lost, the device is able to control breathing by stimulation of the phrenic nerve, diaphragm or intercostals muscle. The parameters (frequency, amplitude, pulse width, etc.) for this stimulation are based on feedback from the physiological sensors. If a first neural stimulation is ineffective at 752, stimulation parameters can be adjusted at 754. If stimulation is still ineffective at 755, an embodiment involves delivering neural stimulation therapy to an alternative neural target, at 756. Not all embodiments use all the described steps.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable medical device, comprising:
 a sensor configured to sense neural activity for chemoreceptors or mechanoreceptors;
 a sensing circuit to receive sensed signals representative of an incidence of a central respiratory disease, wherein the sensed signals include directly sensed neural activity for chemoreceptors or mechanoreceptors;
 a neural stimulator adapted to generate neural stimulation signals; and
 a controller programmed to communicate with the sensing circuit and to control the neural stimulator to stimulate a desired neural target to regulate respiratory neural drive in response to the incidence of the central respiratory disease to treat the central respiratory disease.

2. The implantable medical device of claim 1, wherein the neural stimulator is adapted to stimulate chemoreceptors to treat the central respiratory disease.

3. The implantable medical device of claim 1, wherein the neural stimulator is adapted to stimulate mechanoreceptors to treat the central respiratory disease.

4. The implantable medical device of claim 1, wherein the neural stimulator is adapted to stimulate a vagal nerve to treat the central respiratory disease.

5. The implantable medical device of claim 1, wherein the neural stimulator is adapted to stimulate a glossopharyngeal nerve to treat the central respiratory disease.

6. The implantable medical device of claim 1, wherein the neural stimulator is adapted to stimulate a phrenic nerve to treat the central respiratory disease.

7. The implantable medical device of claim 1, wherein the neural stimulator is adapted to stimulate respiratory centers in a brain to treat the central respiratory disease.

8. The implantable medical device of claim 1, wherein the neural stimulator is adapted to stimulate a diaphragm muscle to treat the central respiratory disease.

9. The implantable medical device of claim 1, wherein the sensed signals include directly sensed neural activity for chemoreceptors and mechanoreceptors.

10. A system, comprising:
   at least one neural stimulation lead having at least one electrode;
   at least one sensor adapted to monitor physiological parameters to detect an incidence of a central respiratory disease, wherein the sensor is configured to sense neural activity for chemoreceptors or mechanoreceptors; and
   an implantable medical device, coupled to the at least one lead and to the at least one sensor, the implantable device including:
      a sensing circuit to receive sensed signals representative of the incidence of the central respiratory disease from the at least one sensor, wherein the sensed signals include directly sensed neural activity for chemoreceptors or mechanoreceptors;
      a neural stimulator adapted to generate neural stimulation signals; and
      a controller programmed to communicate with the sensing circuit and to control the neural stimulator to stimulate a desired neural target to mimic normal chemoreceptor or mechanoreceptor activity in response to the incidence of the central respiratory disease to treat the central respiratory disease.

11. The system of claim 10, wherein the implantable medical device is adapted to provide cardiac rhythm management therapy.

12. The system of claim 10, wherein the at least one sensor is adapted to monitor neural activity of chemoreceptors.

13. The system of claim 10, wherein the at least one sensor is adapted to monitor neural activity of mechanoreceptors.

14. The system of claim 10, wherein the physiological parameters include body movement.

15. The system of claim 10, wherein the physiological parameters include heart rate.

16. The system of claim 10, wherein the physiological parameters include QT interval.

17. The system of claim 10, wherein the physiological parameters include eye movement.

18. The system of claim 10, wherein the physiological parameters include respiration rate.

19. The system of claim 10, wherein the physiological parameters include transthoracic impedance.

20. The system of claim 10, wherein the physiological parameters include tidal volume.

21. The system of claim 10, wherein the physiological parameters include minute ventilation.

22. The system of claim 10, wherein the physiological parameters include blood gas levels.

23. The system of claim 10, wherein the physiological parameters include body temperature.

24. The system of claim 10, wherein the at least one sensor includes a sensor external to a human body.

25. An implantable medical device, comprising:
   a sensor configured to sense neural activity for chemoreceptors or mechanoreceptors;
   a sensing circuit to receive sensed signals representative of an incidence of a central respiratory disease, wherein the sensed signals include directly sensed neural activity for chemoreceptors and mechanoreceptors;
   a neural stimulator adapted to generate neural stimulation signals; and
   a controller programmed to communicate with the sensing circuit and to control the neural stimulator to stimulate a desired neural target to regulate afferent and efferent respiratory neural drive in response to the incidence of the central respiratory disease to treat the central respiratory disease.

* * * * *